United States Patent
Lehner et al.

(10) Patent No.: US 11,275,073 B2
(45) Date of Patent: Mar. 15, 2022

(54) PROBING A STRUCTURE OF CONCRETE BY MEANS OF ELECTROMAGNETIC WAVES

(71) Applicant: PROCEQ SA, Schwerzenbach (CH)

(72) Inventors: Samuel Lehner, Zurich (CH); Ralph Mennicke, Uster (CH)

(73) Assignee: PROCEQ SA, Schwerzenbach (CH)

( * ) Notice: Subject to any disclaimer, the term of this patent is extended or adjusted under 35 U.S.C. 154(b) by 395 days.

(21) Appl. No.: 16/491,929

(22) PCT Filed: Mar. 10, 2017

(86) PCT No.: PCT/CH2017/000028
§ 371 (c)(1),
(2) Date: Sep. 6, 2019

(87) PCT Pub. No.: WO2018/161183
PCT Pub. Date: Sep. 13, 2018

(65) Prior Publication Data
US 2020/0072813 A1    Mar. 5, 2020

(51) Int. Cl.
*G01N 33/38* (2006.01)
*G01N 22/02* (2006.01)

(52) U.S. Cl.
CPC ........... *G01N 33/383* (2013.01); *G01N 22/02* (2013.01)

(58) Field of Classification Search
CPC .................... G01N 22/02; G01N 33/383
See application file for complete search history.

(56) References Cited

U.S. PATENT DOCUMENTS

| | | |
|---|---|---|
| 3,550,442 A | 12/1970 | Carr et al. |
| 5,416,802 A | 5/1995 | Ishii |
| 6,246,354 B1 | 6/2001 | Liedtke et al. |
| 7,019,686 B2 | 3/2006 | Hester et al. |
| 7,224,237 B2 | 5/2007 | Hirano et al. |
| 9,194,819 B2 | 11/2015 | Mulumulla et al. |

(Continued)

FOREIGN PATENT DOCUMENTS

| | | |
|---|---|---|
| CN | 204271694 | 4/2015 |
| CN | 104849290 A | 8/2015 |

(Continued)

OTHER PUBLICATIONS

Morris et al., "Ground Penetrating Radar for Concrete Evaluation Studies", https://www.researchgate.net/publication/252266154 (Year: 2004).*

(Continued)

*Primary Examiner* — Regis J Betsch
(74) *Attorney, Agent, or Firm* — Greenblum & Bernstein, P.L.C.

(57) ABSTRACT

In order to accurately probe a structure of concrete, a series of probe signals with defined carrier frequencies are generated by a probe signal generator and coupled into the structure by an antenna. The returning echo signals are processed by an echo signal receiver. Processing includes phase and amplitude detection in a multiplier, frequency-specific scaling in a scaling unit, replacement of the measured phases and amplitudes in an interpolation unit, and the generation of time-domain data in a Fourier transformation module. The device is robust against RF noise, accurate and low-power.

25 Claims, 1 Drawing Sheet

(56) References Cited

U.S. PATENT DOCUMENTS

| | | | |
|---|---|---|---|
| 9,397,870 B2 | 6/2016 | Kwon et al. | |
| 2002/0057095 A1* | 5/2002 | Zoughi | G01N 33/383 324/646 |
| 2003/0098697 A1* | 5/2003 | Tanaka | G01N 33/383 324/637 |
| 2007/0056374 A1* | 3/2007 | Andrews | G01N 29/4418 73/628 |
| 2016/0103197 A1 | 4/2016 | Schultz et al. | |

FOREIGN PATENT DOCUMENTS

| | | |
|---|---|---|
| EP | 1 739 423 | 1/2002 |
| EP | 1 310 792 | 5/2003 |
| EP | 2 618 140 | 7/2013 |
| GB | 1332898 | 10/1973 |
| GB | 1 591 678 | 6/1981 |
| JP | 2002-357566 | 12/2002 |
| JP | 2003-207463 | 7/2003 |
| JP | 2006-304963 | 11/2006 |
| JP | 2013-148587 | 8/2013 |
| JP | 2014-219238 | 11/2014 |
| RU | 93003258 | 3/1995 |
| RU | 2354977 | 5/2009 |
| WO | 2016/124841 | 8/2016 |

OTHER PUBLICATIONS

Japan Search Report/Office Action conducted in counterpart Japan Appln. No. 2019-548917 (dated Nov. 10, 2020) (w/ translation).

Russia Search Report conducted in counterpart Russia Appln. No. 2019131809/14(062484) (dated Apr. 8, 2020) (w/ translation).

Russia Office Action conducted in counterpart Russia Appln. No. 2019131809/14(062484) (dated May 18, 2020) (w/ translation).

Korea Search Report/Office Action conducted in counterpart Korea Appln. No. 10-2019-7026306 (dated Mar. 22, 2021) (w/ translation).

Int'l Search Report (form PCT/ISA/210) conducted in Int'l Appln. No. PCT/CH2017/000028 (dated Jun. 30, 2017).

Int'l Written Opinion (form PCT/ISA/220 & PCT/ISA/237) conducted in Int'l Appln. No. PCT/CH2017/000028 (dated Jun. 30, 2017).

\* cited by examiner

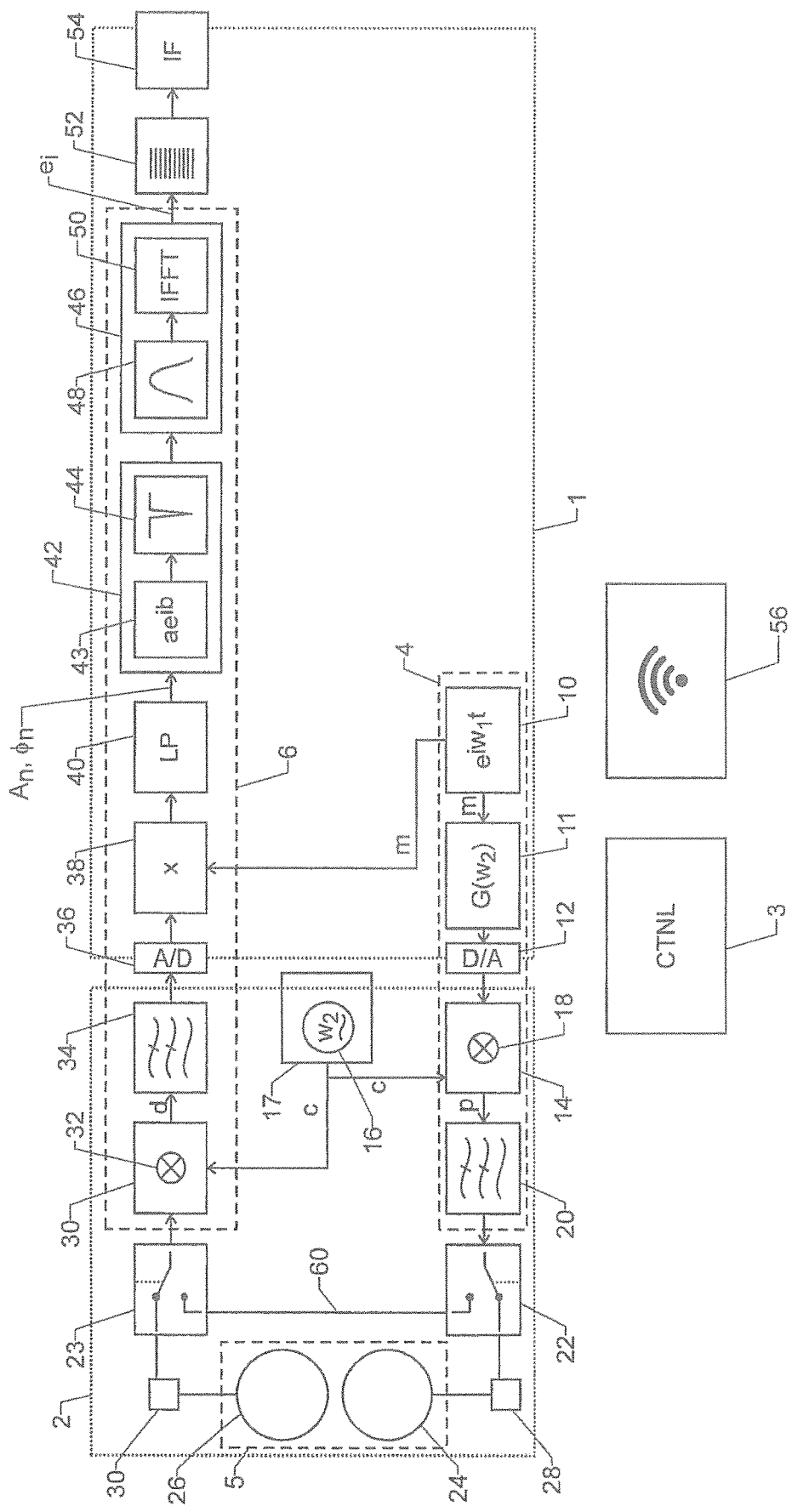

PROBING A STRUCTURE OF CONCRETE BY MEANS OF ELECTROMAGNETIC WAVES

TECHNICAL FIELD

The invention relates to a method for probing a structure of concrete where an electromagnetic wave is sent into the structure, an echo of the wave is received from the structure, and internal features of the structure are derived from the echo.

The invention also relates to a device for carrying out said method.

BACKGROUND ART

It has been known to probe the structure of concrete by means of electromagnetic waves. For doing so, a short electromagnetic pulse is sent into the structure and its echo is received. The structure can then be derived from the amplitude and delay of the peaks in the echo.

This type of analysis requires complex hardware that is able to sample the returning echoes with high temporal resolution. This type of hardware needs to perform a high-frequency sampling of the echo and therefore has high power consumption. Also, signals over a wide frequency range have to be processed, which makes the technology sensitive to interference with radio communication signals, such as WiFi signals.

DISCLOSURE OF THE INVENTION

Hence, it is a general object of the invention to provide a method and device of this type with low power consumption.

This object is achieved by the method and device of the independent claims.

Accordingly, the method for probing a structure of concrete comprises the following steps:
  Sending, by means of an antenna, are electromagnetic wave into the structure.
  Receiving, by means of the antenna, an echo of the electromagnetic wave from the structure.
  Deriving features of said structure from the echo.

Further, the step of sending the electromagnetic wave into the structure comprises, in its turn, the step of subsequently sending a plurality of electromagnetic probe signals of different frequencies into the structure. In other words, a series of electromagnetic probe signals of different frequencies are generated one after the other, and each one of them is sent into the structure to be probed.

The step of receiving the echo comprises, in its turn, the step of receiving an echo signal for each of said probe signals and determining the amplitude and phase for each of the echo signals. In other words, for each probe signal, the amplitude and phase of the returning signal is determined, e.g. by means of determining the real and imaginary parts of the complex amplitude thereof.

The step of deriving the internal features involves using the amplitude and phase shift of said echo signals.

This technique is based on the idea that the pulses of the conventional system can also be replaced by a series of (longer) probe signals, with the probe signals differing from each other in their frequencies. Hence, the measurement is, in some sense, earned out in the frequency domain. Frequency domain data can be analyzed with lower sampling rates, which reduces the technology's power requirements.

The claimed device for carrying out the invention comprises:
  An antenna: The antenna is used for coupling the electromagnetic wave into the concrete structure and for picking up its echo.
  A probe signal generator for generating the electromagnetic wave to be sent into said structure.
  An echo signal receiver for processing the echo from said structure.
  A control unit for controlling the probe signal generator and the echo signal receiver. The control unit is adapted and structured to carry out the method according to the present invention.

Advantageously, the probe signals each comprise a carrier signal modulated by a modulation signal. The frequency of the carrier signal is at least 100 MHz and the frequency of the modulation signal is no more than 10 MHz. The individual probe signals differ in the frequency of their carrier signals, i.e. the carrier signal frequency is varied between subsequent probe signals.

The echo signals are then demodulated at the frequency of the carrier signal, i.e. the modulated signal is extracted for each echo signal by means of demodulation.

This has the advantage that the demodulated signal is not a DC signal, which makes it more robust against drift and 1/f-noise.

Advantageously, the frequency of the modulation signal is at least 0.5 MHz because 1/f-noise is low at such frequencies and because crosstalk signals are outside the analyzed spectrum.

In another advantageous embodiment, the frequency of the modulation signal is the same for all said probe signals. This simplifies the generation and the demodulation of the signals.

The device advantageously comprises:
  An analogue modulator for modulating a carrier signal with a modulation signal in order to generate the probe signals. The frequency of the carrier signal is at least 100 MHz and the frequency of the modulation signal is no more than 10 MHz. The different probe signals differ in the frequency of their carrier signals.
  An analog demodulator for demodulating the echo signals at the frequency of the carrier signal. The signal demodulated in this manner is called the "demodulated echo signal". Advantageously, the demodulator comprises a multiplier for multiplying the echo signals with a signal having the frequency of the carrier signal.

By carrying out the modulation and demodulation in analogue circuitry, the power consumption and clock frequency of the digital circuitry can be reduced further.

Advantageously, the demodulated echo signal is fed to an analog-digital-converter for converting it to digital values. The device further comprises a signal processor for digitally processing these digital values. This is based on the understanding that the frequency of the demodulated signal is sufficiently low for efficient, accurate and low-power digital processing.

The method advantageously comprises the further step of determining a set of amplitudes and phases of the different echo signals, which can then be used for a further analysis. Each amplitude and phase of this set describes the amplitude and phase of one frequency of the probe signals.

The amplitude and phase can be determined explicitly (e.g. in Volts and radian), or in the form of a parameter from which the explicit amplitude and phase can be calculated (such as a complex value whose absolute value is proportional to the amplitude and whose phase describes the phase of the signal), respectively.

Advantageously, the method further comprises the step of individually filtering the amplitude and/or phase of each echo signal. In this context, filtering implies a mapping of the amplitude or phase to a new, filtered value. And "individually" filtering implies that this mapping depends on the frequency of the corresponding probe signal that gave rise to the given echo signal.

In particular, the phase can be shifted by a phase offset and/or the amplitude can be scaled by a scale factor, where the phase offset and the scale factor depend on the frequency of the corresponding probe signal (i.e. of the echo signal that had the given amplitude and/or phase). Such individual filtering has various applications:

a) In a first application, this filtering can be used for compensating the measurement for the frequency response of the components of the device. In this case, the invention comprises the steps of providing calibration data descriptive of the frequency response of the device used for carrying out the method, and using this calibration data in said filtering step for compensating for the frequency response.

b) In a second application, the filtering can be used for weighing the data corresponding to the individual probe signal frequencies before Fourier-transforming them. This allows to generate a simulated time-domain response signal for an arbitrary simulated time-domain probe signal. The weighing can also be used to improve the stop-band attenuation. In this case, the invention comprises the steps of providing a series of Fourier amplitudes and phases descriptive of Fourier transforms of a desired time-domain probe signal, and using said Fourier amplitudes and phases in said filtering step for generating a simulated time-domain response signal.

In yet another advantageous embodiment, the invention comprises the step of replacing a subset of the set of amplitudes and phases by estimated amplitudes and/or phases. This allows to remove individual frequency components from the received signal, in particular the components subject to strong noise. This is particularly useful for suppressing the typical WiFi frequencies. Hence, advantageously, at least some of the subset of replaced amplitudes and phases are descriptive of probe signals having frequencies between 2.4 and 2.4835 GHz and/or between 5.15 and 5.35 GHz and/or between 5.47 and 5.725 GHz.

Advantageously, the method comprises the step of calculating the estimated amplitudes and/or phases using interpolation and/or extrapolation from amplitudes and phases that are not part of said subset.

In yet another advantageous embodiment the method comprises the following steps:

Providing a set of frequency-dependent probe signal amplitudes descriptive of signal amplitudes of said probe signals. In this context, the term "frequency-dependent" implies that not all probe signals at the various frequencies have the same amplitude.

Using said probe signal amplitudes for individually controlling the signal amplitudes of the probe signals.

In this manner, it is possible to vary the amplitudes of the individual probe signals as a function of their frequency. This allows to reduce the spectral noise at frequencies where legal or technical requirements imply that emissions are to be low.

BRIEF DESCRIPTION OF THE DRAWING

The invention will be better understood and objects other than those set forth above will become apparent when consideration is given to the following detailed description thereof. This description makes reference to the annexed drawing, which shows a block circuit diagram of a device for electromagnetically probing a structure of concrete.

MODES FOR CARRYING OUT THE INVENTION

Overview:

The device of FIG. 1 comprises a first section 1 of digital processing circuitry and a second section 2 of analogue processing circuitry.

First section 1 is advantageously formed by an FPGA circuit or some other circuit technology allowing to implement sequential logic.

The device further comprises a control unit 3, which may be implemented, at least partially, as part of first section 1 and/or as a separate, digital device, such as a microprocessor.

The most important parts of the device described here are:

A probe signal generator 4 adapted and structured to generate an electromagnetic wave to be sent into the structure to be probed.

An antenna 5 for coupling the electromagnetic wave into the structure and for receiving an echo therefrom.

An echo signal receiver 6 adapted and structured to process the echo.

The function and design of these parts are described in more detail in the following sections.

Probe Signal Generator:

Probe signal generator 4 comprises a modulation signal source 10. It is advantageously implemented as a digital oscillator in first section 1. It generates a series of modulation signal values m, which are advantageously represented as a time series of complex numbers $$m = e^{i\omega_1 t}, \quad (1)$$

where $\omega_1$ is called the modulation frequency. This frequency is advantageously no more than 10 MHz, in particular no more than 5 MHz, in order to make the modulation signal values easy to process in low-power digital circuitry. On the other hand, $\omega_1$ is advantageously larger than 0.5 MHz in order to be in a range where the 1/f-noise of analog section 2 is low and crosstalk signals are outside the analyzed spectrum. In an advantageous embodiment, the modulation frequency $\omega_1$ is 2 MHz.

The series of values m can, as will be clear to the skilled person, e.g. be represented as a series of the real and imaginary parts of the complex values, or as a series of amplitude and phase values.

The modulation signal values in are fed to a scaler 11. It generates a series of scaled modulation signal values m'

$$m' = G(\omega_2) \cdot m, \quad (2)$$

where $G(\omega_2)$ are scale factors that vary a carrier frequency $\omega_2$. The scale factors $G(\omega_2)$ define the amplitudes of the probe signals and allow these amplitudes to vary for differing carrier frequencies $\omega_2$. The role of the carrier frequency $\omega_2$ will be described in more detail below.

The carrier-frequency-dependent scaling achieved by scaler 11 allows to reduce the amplitude of the probe signals for those carrier frequencies where spectral emissions of the device must be low.

Scaler 11 is optional. If it is omitted, we have m'=m (optionally scaled with a constant value).

The scaled modulation signal values m' are fed to a digital-analog-converter 12, which e.g. generates analog signals representing the real and imaginary part of m'.

The signals from converter 12 are fed to a modulator 14, where the are mixed with a carrier c having the carrier frequency $\omega_2$ in order to generate a probe signal p comprising a carrier signal modulated by the modulation signal.

The carrier c is generated by an analogue oscillator 16, whose frequency $\omega_2$ can be controlled by control unit 3.

Analogue oscillator 16 is advantageously part of a programmable frequency synthesizer 17, in particular the VCO of such a synthesizer. An example of a suitable circuit is e.g. ADF4351 by Analog Devices, Inc.

As mentioned, the carrier frequency $\omega_2$ is advantageously at least 100 MHz. Control unit 3 varies it over time in order to generate a sequence of N electromagnetic probe signals with N differing frequencies $\omega_{2,1} \ldots \omega_{2,N}$.

Modulator 14 is advantageously an IQ-mixer (IQ-modulator) comprising a modulation-multiplier 18 for multiplying carrier c with suitable phase-shifted values of the analogue modulation signal values m'.

As mentioned, the probe signal p generated by modulator 14 is basically the carrier signal c modulated by the (lower frequency) modulation signal m'.

Probe signal p is sent through a probe signal filter 20 in order to cut off the harmonic frequencies of carrier frequency $\omega_2$. Advantageously, probe signal filter 18 is a programmable low-pass filter whose cut-off frequency can be set by control unit 3.

The filter probe signal passes a first switch 22, from where it can selectively be sent to antenna 5 or to a second switch 23. First and second switch 22, 23 are used for calibrating the device. This will be described in further detail in the section Device Calibration, below.

Antenna:

Antenna 5 advantageously uses a plate-loaded design, e.g. with two circular disks 24, 26, one for sending the electromagnetic wave into the concrete structure to be sampled, and one for receiving its echo. Instead of a pair of circular disks, a bow tie design or any other suitable broadband antenna design can be used.

Matching circuits 28, 30, for matching impedances and/or signal levels, can be provided between the antenna elements and probe signal generator 4 at the input side as well as between the antenna elements are echo signal receiver 6 at the output side.

Echo Signal Receiver:

Before entering echo signal receiver 6, the echo signals pass second switch 23.

The echo signal is then fed to a demodulator 30, which forms part of echo signal receiver 6. Advantageously, demodulator 30 is an analogue circuit in order to be able to process high frequency signals with low power consumption.

Demodulator 30 preferably comprises a demodulation-multiplier 32, where the echo signal is multiplied with the carrier c from oscillator 16 in order to demodulate it and to generate a demodulated echo signal d.

Demodulated echo signal d is advantageously passed through an analog echo signal filter 34 adapted to at least suppress signals above modulation frequency $\omega_1$ but not the signals at modulation frequency $\omega_1$. Echo signal filter 34 can be a low-pass or a band-pass filter. Using a low-pass filter is preferred, though, for its faster settling time, which makes it possible to use shorter probe pulses.

After signal filter 34, demodulated echo signal d is basically an alternating signal at modulation frequency $\omega_1$. Its amplitude will depend on how strongly the probe signal was reflected by the concrete structure, and its phase will be descriptive of the phase shift between the probe signal and the echo signal.

In addition to the components shown in FIG. 1, the analog circuitry of echo signal receiver 6 can comprise suitable analog amplifiers and filters.

The demodulated echo signal d is then fed to an analog-digital-converter 36 and enters the digitally implemented part of echo signal receiver 6, which forms a signal processor for digitally processing the demodulated echo signal d.

This signal processor comprises a multiplier 38 for multiplying the demodulated echo signal d with the modulation signal m in order to determine the amplitude and phase of the demodulated echo signal d at the frequency $\omega_1$ of the modulation signal m. This amplitude A and phase $\varphi$ are directly dependent on the phase shift of the echo signal in respect to the probe signal and on the reflection strength of the echo signal. However, they also depend on the inherent properties of the analogue circuitry the signals have passed through, and they may be affected by noise. Hence, further steps are carried out for processing the amplitude and phase A, $\varphi$.

In a next step, the amplitude and phase values are passed through a low-pass filter 40. This filter advantageously integrates the values of the amplitude and phase over at least 50% and/or no more than 90% of the length of a single probe signal. For probe signals of a duration of 2 µs, low pass filter 40 may integrate (i.e. average) the signals over the time span of e.g. 1.5 µs.

The averaged amplitude and phase A, $\varphi$ at the output of low-pass filter 40 can be downsampled, if necessary, to one value per probe signal.

The amplitude and phase A, $\varphi$ differ between subsequent probe signals as a function of the carrier frequency $\omega_{2,n}$ of the probe signals. Hence, in the following, they are denoted by an index n, i.e. $A_n$, $\varphi_n$, with n=1 . . . N standing for the index of the probe signal.

The amplitudes and phases $A_n$, $\varphi_n$ of the individual probe signals are submitted to a frequency-selective filtering unit 42, which is adapted and structured to individually filtering the amplitude and/or phase of the echo signal for each probe signal. In other words, filtering unit 42 corrects the amplitude and phase for each of the frequencies $\omega_{2,n}$ (with n=1 . . . N) of the probe signals.

In the embodiment shown in FIG. 1, filtering unit 42 carries out two such filtering operations.

In a first step, in a scaling unit 43, each amplitude and/or phase is scaled and/or offset. When expressing the amplitudes and phases as complex numbers $$Z_n = A_n \cdot e^{i\varphi_n}, \qquad (3)$$

the scaling and offset can be carried out by a multiplication $$Z'_n = Z_n \cdot a_n \cdot e^{ib_n}, \qquad (4)$$

with $Z'_n$ being the corrected amplitude and phase, $a_n$ being the amplitude correction of the probe signal of frequency $\omega_{2,n}$ and $b_n$ being the phase correction of the probe signal of frequency $\omega_{2,n}$. The phase offset $b_n$ and the scale factor $a_n$ are functions of the frequency $\omega_{2,n}$ of the respective probe and echo signals.

The correction of Eq. (4) is particularly advantageous for compensating device properties, as will be described in the section Device Calibration below.

In a next step, the amplitudes and phases can optionally be fed to an interpolation unit 44. This interpolation unit is adapted and structured to replace a subset of said set of amplitudes and phases $A_n$, $\varphi_n$ by estimated amplitudes and/or phases.

As mentioned above, the purpose of the interpolation unit 44 is to ignore individual frequencies are $\omega_{2,n}$. For example, if one of these frequencies, e.g. $\omega_{2,k}$, falls into a band used for WiFi communication, especially for WiFi communication presently used by the device, it may carry a major noise and spurious level. In this case, it is best to replace the respective amplitudes and phases $A_k$, $\omega_k$, with estimated values $A'_k$, $\varphi'_k$. In a simple case, if $k>1$ and $k<N$ and if the frequencies $\omega_n$ are evenly spaced apart, a linear interpolation can e.g. be used $$A'_k = (A_{k+1} + A_{k-1})/2, \quad (5a)$$

$$\varphi'_k = (\varphi_{k+1} + \varphi_{k-1})/2, \quad (5b)$$

For $k=1$ or $k=N$, linear extrapolation can be applied. Alternatively to using linear interpolation or extrapolation, more sophisticated methods of interpolation can be used, e.g. based on higher order polynomials, splines or curve fitting techniques. In yet another alternative, interpolation unit 44 can set a weight of the signals at said individual frequencies $\omega_{2,n}$ to zero, in a technique similar to as it is used for notch filters.

In more general terms, the estimated amplitudes and/or phases $A'_k$, $\varphi'_k$ are calculated using interpolation and/or extrapolation from the amplitudes and phases that are not part of the subset to be replaced.

Now, the set amplitudes and phases $A_n$, $\varphi_n$ as processed by sealing unit 43 and/or interpolation unit 44 can be used to derive information about the concrete structure that has been probed. Techniques for doing so are known to the skilled person.

However, advantageously, the set amplitudes and phases $A_n$, $\varphi_n$, which describe the reflectivity of the sampled structure in the frequency domain, are first transformed into a time-domain response signal by subjecting them to a Fourier transform. This is because many the tools used for processing reflection data of concrete samples are based on analyzing time-domain data, i.e. on analyzing the echo amplitude of a short pulse sent into the structure (A-scan analysis).

This step can be carried out by a Fourier transformation module 46. It comprises a spectral filter unit 48 and an inverse-Fourier-transform unit 50.

Spectral filter unit 48 scales the amplitudes $A_n$ by reducing the weight of the low- and high-end spectral components. This can be carried out in a unit similar to scaling unit 43, i.e. each spectral component of the phases $A_n$, $\varphi_n$ can be multiplied by complex scaling values $S_n$.

For example, $S_n$ can be defined as follows:

$$S_n = \frac{1}{2}\left[1 - \cos\left(\frac{2\pi n}{N-1}\right)\right]$$

This function describes a weighted window. For example, a Harn window of a Tukey window can be used. In this case, $S_n$ is real-valued and applied to both the real and imaginary part of the complex amplitude-phase values.

The purpose of spectral filter unit 48 is to scale the spectral amplitudes (and, optionally, to offset the phases) in such a manner that they represent the Fourier transform of a short wavelet as it is generated by conventional pulse-probing devices. The weighing can also be used to improve the stop-band attenuation.

In a next step, the amplitudes and phases $A_n$, $\varphi_n$ scaled in spectral filter unit 48 are submitted to an inverse Fourier transform in inverse-Fourier-transform unit 50. This generates a time-series $e_i$ of an echo as it would be returned when sending the wavelet used for calculating the scaling values $S_n$ into the concrete structure.

The resulting time-series $e_i$ and/or the amplitudes and phases $A_n$, $\varphi_n$ as processed by scaling unit 43 and/or interpolation unit 44 can then be stored in a buffer 52, which can be read-out via an interface 54.

The device of FIG. 1 further can comprise a WiFi interface 56 for wireless communication, in particular for wireless communication based on at least one of the IEEE 802.11 standards. Thanks to the selective frequency component interpolation/extrapolation provided by interpolation unit 44, the operation of WiFi interface 56 does not interfere with the measurements.

WiFi interface 56 can e.g. be used by external devices for accessing data through interface 54 and/or for communicating with control unit 3.

Operation:

As already mentioned above, control unit 3 operates the device for generating a series of electromagnetic probe signals with carrier frequencies $\omega_{2,1} \ldots \omega_{2,N}$, each one of them modulated with modulation frequency $\omega_1$.

Advantageously, the number N of different probe signals is large enough for a good resolution and range, e.g. $N \geq 190$, in particular $N \geq 380$.

The carrier frequencies $\omega_{2,n}$ advantageously span a spectral range exceeding 3.8 GHz.

For example, the spectral range of the carrier frequencies $\omega_{2,n}$ extends between 200 MHz and 4 GHz.

Advantageously, the carrier frequencies $\omega_{2,n}$ are evenly spaced over their spectral range, e.g. in steps of 10, 20 or 40 MHz. In a particularly advantageous embodiment, the user can select the step width in order to find the desired tradeoff between resolution (range) and measurement rate.

The duration of each probe pulse advantageously is at least one period of the modulation frequency. Taking into account that the various filters need some time to settle, it is best chosen to exceed 2 times the period of the modulation frequency, e.g. to be equal to 3 times this period. For a modulation frequency $\omega_1 = 2$ MHz, the duration of each pulse is e.g. 2 µs (which equals four times the period).

For each probe pulse n, control unit 3 sets the following parameters:

The frequency $\omega_{2,n}$ of oscillator 16.
The value $G(\omega_{2,n})$ to be used by scaler 11.
The cut-off frequency of probe signal filter 20 such that it is higher than $\omega_{2,n}$ but lower than $2 \cdot \omega_{2,n}$.
The amplitude correction $a_n$ and the phase correction $b_n$ to be used in scaling unit 43.
The settings of the interpolation unit 44. These settings can be derived from invariant, constant information, e.g. based on the knowledge of which frequency bands are subject to strong signal noise. Alternatively, the device can dynamically measure or determine the surrounding RF noise, e.g. by scanning it with a radio receiver and/or by deriving noisy frequency bands from the current operation of WiFi interface 56. Depending on this measured or determined RF noise, the settings of interpolation unit 44 can be adapted to the current operating conditions.

Upon completion of all N probe pulses, the time domain signal can be calculated by Fourier transformation module 46 and stored in buffer 52, together with the amplitudes and phases $A_n$, $\varphi_n$.

Device Calibration:

As mentioned, scaling unit 43 can be used for compensating device properties. In particular, the components of the analog section 2 of the present device, such as the probe signal filter 20, echo signal filter 34 and the various amplifiers (not shown) will introduce phase delays as well as gain variations that depend on the carrier frequency $\omega_{2,n}$.

If, for example, these effects lead to a phase offset $\delta_n$ and a gain $q_n$ at carrier frequency $\omega_{2,n}$, probe signal filter 20 can be set to correct the amplitudes and phases $A_n$, $\omega_n$ in Eq. (4) by using $a_n = 1/q_n$ and $b_n = -\delta_n$.

In other words, the phase offset $\delta_n$ and gain $q_n$ are calibration data describing the frequency response of the device, and they can be used for filtering the amplitudes and phases $A_n$, $\omega_n$.

The calibration parameters may be derived from theoretical considerations and/or from measurements on sample devices. However, advantageously, the device can be equipped with its own means to determine the calibration data dynamically and repetitively. This allows to compensate for drift effects due to device aging and varying environmental conditions.

In the embodiment of FIG. 1, the device is equipped with a calibration unit comprising the first and second switches 22, 23 for bypassing antenna 5. FIG. 1 shows these switches in their measurement position. However, control unit 3 can move them into a calibration position, in which case the probe signals bypass antenna 5 and are sent through a shunt line 60 directly to echo signal receiver 6.

In order to calibrate the device, control unit 3 moves the switches 22, 23 into their calibration positions, and then it causes probe signal generator 4 to generate a series of N probe pulses with carrier frequencies $\omega_{2,1} \ldots \omega_{2,N}$ just as during a regular measurement, but it sets $a_n$ and $b_n$ of scaling unit 43 to constant values, e.g. 1 and 0, respectively. This allows the device to measure the calibration data $\delta_n$ and $q_n$. Optionally, these can be subjected to an additional, factory-defined correction for the frequency response of antenna 5 and its matching circuits 28, 30.

Notes:

As mentioned above, first digital section 1 of the present device is advantageously an FPGA. It advantageously contains the components used for generating the modulation signal at frequency $\omega_1$, i.e. modulation signal source 10 and (if present) scaler 11. It also comprises multiplier 38, which allows to perform a highly sensitive and accurate phase detection of the echo signals. The FPGA can further comprise the components of signal receiver 6 that process the phases and amplitudes $A_n$, $\varphi_n$ from multiplier 38.

Circuits processing the signals at the carrier frequencies $\omega_{2,n}$, on the other hand, are advantageously analog circuits, in particular the multipliers 18, 32, the oscillator 16, and the filters 20, 34.

In summary, the device shown here is able to accurately probe a structure of concrete with low power consumption. To do so, it generates a series of probe signals with defined carrier frequencies by means of probe signal generator 4. The probe signals are coupled into the structure of concrete by means of an antenna 5. The returning echo signals are processed by an echo signal receiver 6. Processing includes phase and amplitude detection in a multiplier 38, frequency-specific scaling in a sealing unit 43, replacement of the measured phases and amplitudes in an interpolation unit 44, and the generation of time-domain data in a Fourier transformation module 46. Its design makes the device robust against RF noise and accurate, and its architecture allows for implementations with low power consumption.

While there are shown and described presently preferred embodiments of the invention, it is to be distinctly understood that the invention is not limited thereto but may be otherwise variously embodied and practiced within the scope of the following claims.

The invention claimed is:

1. A method for probing a structure of concrete, said method comprising:
   sending an electromagnetic wave into said structure by an antenna,
   receiving an echo of said electromagnetic wave from said structure by said antenna,
   deriving internal features of said structure from said echo, wherein
   said sending the electromagnetic wave into said structure comprises subsequently sending a plurality of electromagnetic probe signals of different frequencies into said structure,
   said receiving said echo comprises receiving an echo signal for each of said probe signals and determining an amplitude and phase for each of said echo signals, and
   said deriving the internal features comprises deriving the internal features using said amplitude and phase of said echo signals.

2. The method of claim 1 wherein said probe signals are generated by an analogue oscillator with adjustable frequency.

3. The method of claim 2 wherein said echoes are demodulated in an analogue demodulation-multiplier where they are multiplied with a signal from said analogue oscillator.

4. The method of claim 1 wherein
   said probe signals each comprise a carrier signal modulated by a modulation signal, wherein a frequency of said carrier signal is at least 100 MHz and a frequency of said modulation signal is no more than 10 MHz, and wherein the probe signals differ in the frequency of their carrier signals, and
   said echo signals are demodulated at the frequency of the carrier signal.

5. The method of claim 4, wherein the frequency said modulation signal is larger than 0.5 MHz and/or smaller than 5 MHz.

6. The method of claim 4 wherein the frequency of the modulation signal is the same for all said probe signals.

7. The method of claim 4 wherein said echo signals are demodulated in an analog demodulator, in particular in a multiplier where they are multiplied with a signal having the frequency of the carrier signal, in order to generate a demodulated signal, wherein said demodulated signal is converted to digital values and processed digitally.

8. The method of claim 1 further comprising determining a set of amplitudes and phases of said echo signals.

9. The method of claim 8 further comprising individually filtering the amplitude and/or phase of each echo signal for each probe signal, and in particular wherein the phase is shifted by a phase offset and/or the amplitude is scaled by a scale factor, where the phase offset and the scale factor depend on the frequency of the corresponding probe signal.

10. The method of claim 9 comprising
    providing calibration data descriptive of a frequency response of a device used for carrying out the method, and using said calibration data in said filtering step for compensating for said frequency response.

11. The method of claim 10 comprising measuring said calibration data by bypassing said antenna and operating said device to measure said calibration data.

12. The method of claim 9 comprising
providing a series of Fourier amplitudes and phases descriptive of Fourier transforms of a desired time-domain probe signal, and
using said Fourier amplitudes and phases in said filtering for generating the simulated time-domain response signal.

13. The method of claim 8 comprising subjecting said set of amplitudes and phases to a Fourier transform in order to calculate a simulated time-domain response signal.

14. The method of claim 8 further comprising replacing a subset of said set of amplitudes and phases by estimated amplitudes and/or phases,
and in particular wherein at least some of the subset of amplitudes and phase are descriptive of probe signals having frequencies between 2.4 and 2.5 GHz and/or between 3.5 and 3.7 GHz and/or between 4.94 and 5.99 GHz and/or between 5.25 and 5.35 GHz and/or between 5.47 and 5.73 GHz.

15. The method of claim 14 comprising calculating said estimated amplitudes and/or phases using interpolation and/or extrapolation from amplitudes and phases that are not part of said subset.

16. The method of claim 1 comprising the steps of
providing a set of frequency-dependent probe signal amplitudes descriptive of signal amplitudes of said probe signals, and
using said probe signal amplitudes for individually controlling the signal amplitudes of said probe signals.

17. A device for carrying out the method of claim 1 comprising,
an antenna,
a probe signal generator for generating the electromagnetic probe signals to be sent into said structure through said antenna,
a echo signal receiver for processing said echo signals received from said structure through said antenna,
a control unit for controlling said probe signal generator and said echo signal receiver,
wherein said control unit is adapted and structured to carry out the method of any of the preceding claims.

18. The device of claim 17 further comprising an analogue oscillator with adjustable frequency for generating said probe signals.

19. The device of claim 18 further comprising an analogue demodulation-multiplier for multiplying the echo signals with a signal from said analogue oscillator.

20. The device of claim 17 further comprising
an analogue modulator for modulating a carrier signal with a modulation signal in order to generate said probe signals, wherein a frequency of said carrier signal is at least 100 MHz and a frequency of said modulation signal is no more than 10 MHz, and wherein the probe signals differ in the frequency of their carrier signals, and
an analog demodulator, for demodulating said echo signals at the frequency of the carrier signal in order to generate a demodulated echo signal, and in particular wherein said demodulator comprises a multiplier for multiplying said echo signals with a signal having the frequency the carrier signal.

21. The device of claim 20 further comprising an analog-digital-converter for converting said demodulated echo signal to digital values and a signal processor for digitally processing said demodulated echo signal.

22. The device of claim 20, further comprising a multiplier for multiplying said demodulated echo signal with said modulation signal in order to determine an amplitude and phase of said demodulated echo signal at the frequencies of the modulation signal.

23. The device of claim 20 further comprising an analog echo signal filter processing a signal from said analog demodulator and adapted to at least suppress signals above the frequency of said modulation signal but not signals at the frequency of said modulation signal.

24. The device of claim 17 further comprising
a scaling unit for correcting measured amplitudes and phases of said echo signals by a phase offset and/or a scale factor, where the phase offsets and the scale factors are a function of the frequency of the respective echo signal, and
a calibration unit for bypassing said antenna,
wherein said control unit is structured and adapted to measure calibration data descriptive of its frequency response and to use them for determining the phase offsets and the scale factors.

25. The device of claim 17 further comprising a WiFi interface for wireless communication.

* * * * *